United States Patent [19]

Bollen et al.

[11] Patent Number: 4,692,556
[45] Date of Patent: Sep. 8, 1987

[54] REPEATING TEMPERATURE SENSING IMMERSION PROBE

[75] Inventors: Theo P. C. Bollen, Genk, Belgium; John E. Cassidy, Churchville, Pa.

[73] Assignee: Electro-Nite Company, Philadelphia, Pa.

[21] Appl. No.: 843,436

[22] Filed: Mar. 24, 1986

Related U.S. Application Data

[63] Continuation-in-part of Ser. No. 626,498, Jun. 29, 1984, Pat. No. 4,645,865.

[30] Foreign Application Priority Data

Nov. 22, 1985 [DE] Fed. Rep. of Germany ....... 3541326

[51] Int. Cl.[4] .............................................. H01L 35/02
[52] U.S. Cl. ...................................... 136/234; 136/232
[58] Field of Search ................................. 136/224-234

[56] References Cited

U.S. PATENT DOCUMENTS

| | | | |
|---|---|---|---|
| 3,816,183 | 6/1974 | Kraus | 136/234 |
| 4,093,193 | 6/1978 | Cassidy et al. | 266/87 |
| 4,396,792 | 8/1983 | Falk | 136/234 |
| 4,521,639 | 6/1985 | Falk | 136/234 |

OTHER PUBLICATIONS

Cure et al., Ser. No. 780,707, Jan. 1986.

Primary Examiner—Deborah L. Kyle
Assistant Examiner—T. J. Wallen
Attorney, Agent, or Firm—Seidel, Gonda, Goldhammer & Abbott

[57] ABSTRACT

A temperature sensing device suitable for repeated immersions into a molten metal bath. The invention including a protective refractory sleeve which encases a portion of a generally cylindrical cardboard support tube. Within the suppprt tube is mounted a temperature sensing unit including a body portion, which is positioned within the end of the support tube, and a thermocouple extension portion, which includes a U-shaped quartz tube and which extends through and projects away from the end of the protection sleeve. The cardboard support tube is wrapped with a reflective foil substantially over its end and its entire peripheral surface. The U-shaped quartz tube is provided with an alumina coating to prevent degradation of the quartz material during repeated immersions into the molten metal bath. The combination increasing the number of useful immersions of the sensing unit prior to failure.

11 Claims, 2 Drawing Figures

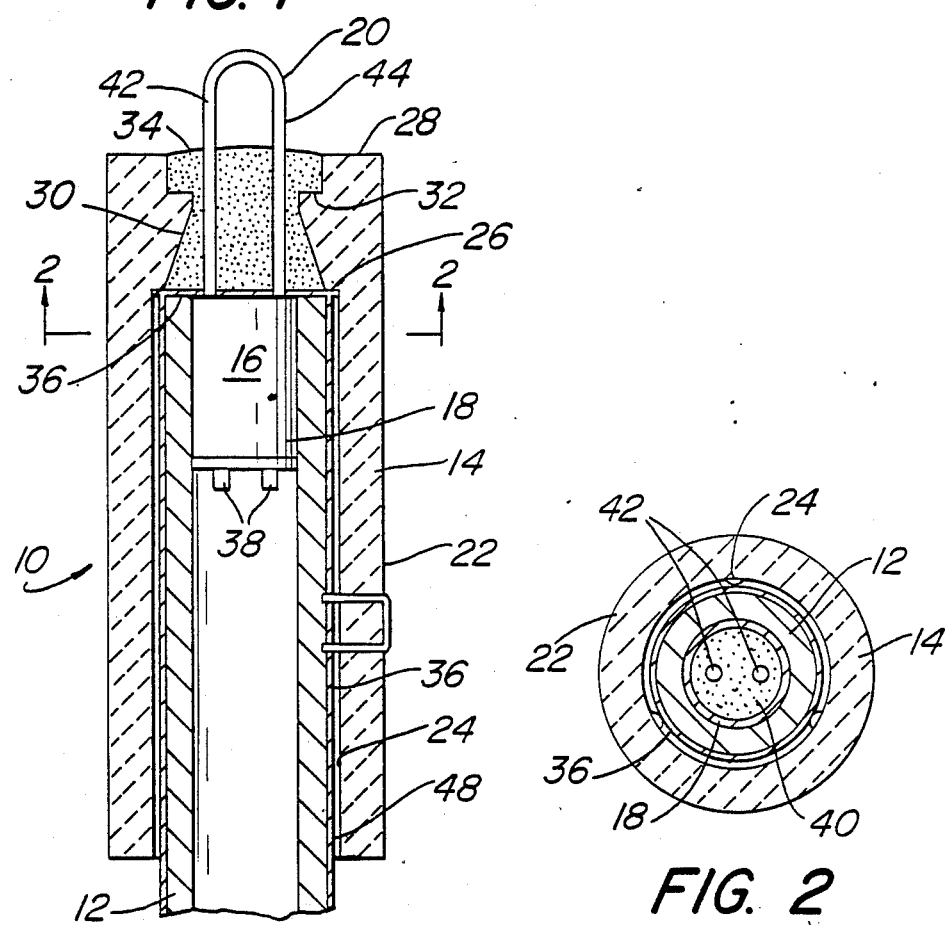

REPEATING TEMPERATURE SENSING IMMERSION PROBE

This is a continuation-in-part of co-pending application Ser. No. 626,498 filed June 29, 1984, now U.S. Pat. No. 4,645,865.

BACKGROUND OF THE INVENTION

This invention relates generally to temperature sensing devices which are suitable for repeated immersions into molten metal. In particular this inventions relates to improvements to a molten metal temperature sensing device which includes a high temperature protection tube of a fiberous refractory material.

As shown by Kraus, U.S. Pat. Nos. 3,816,183, and Falk, No. 4,521,639, it is known to surround a temperature sensing device with a cylindrical sleeve of refractory material for achieving repeated immersions into a molten metal bath. The co-pending application referred to above shows a refractory sleeve having a generally cylindrical bore initiating at one end and terminating at an inwardly projecting shoulder and a tapered or truncated cone shape cylindrical bore which extends from the shoulder through the opposite end of the sleeve.

The construction of the repeating device includes a support tube surrounding a thermocouple unit which is inserted into the cylindrical bore of the refractory sleeve. A projecting portion of the thermocouple unit extends through the cone shaped bore and away from the end of the sleeve by a predetermined distance. The refractory sleeve is secured to the support tube by filling the end of the sleeve with a refractory cement.

The invention described herein is an improvement over the structures shown and described in the previous mentioned patents and pending application so as to further increase the number of immersions that the sensing device may be utilized prior to failure.

SUMMARY OF THE INVENTION

In accordance with the present invention, a preformed refractory sleeve, preferably having a generally cylindrical bore therethrough, is provided for receiving a support tube having a thermocouple unit inserted therein. This structure is further provided, first, with a reflective metal foil which is wrapped around the exterior of the support tube prior to insertion into the preformed refractory sleeve. Second, the quartz tube of the thermocouple unit within the device, which surrounds the hot junction of the thermocouple wire, is provided with an alumina coating. These individual features on a repeating type sensing device or each feature, in conjunction with the other improvement, permit the device to be immersed into a molten metal bath for temperature measurements for an increased number of readings prior to failure, as compared to known structures.

The reflective foil wrap around the, typically, paperboard tube reflects radiant heat prior to and during immersion into the bath. Additionally, the foil wrap protects the paperboard tube such that the temperature seen by the tube is substantially uniform across the length of the tube which is inserted within the refractory sleeve. The foil wrap also seals the outer surface of the paperboard tube so as to limit the amount of oxygen that is in contact with the paperboard tube during immersion. Since the presence of oxygen is removed combustion of the tube at elevated temperatures in basically eliminated.

The alumina coating on the quartz sleeve of the thermocouple unit is provided to eliminate degradation of the quartz material after repeated immersions into the molten metal environment. A common mode of failure in the typical repeating type immersion sensing devices is the failure of the quartz material of the thermocouple tube. It was previously known to coat a thermocouple tube with an alumina coating in a non-repeating device for use in conjunction with a oxygen sensing electrochemical cell which was also mounted on the immersion end of the probe. An example of this type immersion probe is described in Cure, U.S. Pat. No. 4,342,633 and commonly assigned co-pending U.S. patent application Ser. No. 780,707. The coating found on the oxygen and temperature measuring type device is generally heavier than that contemplated by the present invention. The purpose of the alumina coating on this oxygen and temperature type probe is to prevent dissociation of the oxygen in the area of the oxygen sensing electrochemical cell from the quartz material such that the cell provides a more accurate reading of the oxygen content of the molten metal bath. An oxygen and temperature sensing probe is not utilized repeatedly as in the present invention. Additionally, the relatively heavier coating of alumina on the quartz material of the oxygen and temperature type probe slows the time required to make an accurate temperature reading by the thermocouple and, therefore, is undesirable for purposes of a repeating type temperature probe. A repetitive type probe must provide a temperature reading as quickly as possible in order to prevent excessive degradation of its entire structure during a lengthy immersion. The faster the response time of the thermocouple unit the more likely that the number of immersions of the probe will increase prior to a failure.

Further advantages of the invention will become apparent to those skilled in the art by particularly pointing out and describing a perferred embodiment of the invention.

For the purpose of illustrating the invention, there is shown in the drawings a form which is presently preferred; it being understood, however, that this invention is not limited to the precise arrangements and instrumentalities shown.

BRIEF DESCRIPTION OF THE DRAWINGS

FIG. 1 shows a cross sectional view of a repeating high temperature immersion probe of the invention.

FIG. 2 shows a cross sectional view of the immersion probe in FIG. 1 taken along line 2—2.

DETAILED DESCRIPTION OF THE INVENTION

Referring to the drawings wherein like numerals indicate like elements, there is shown in FIG. 1 a cross section of a temperature sensing device 10 which is adapted to be mounted on the immersion end of the lance (not shown). The structure of the device 10 is designed for repeated immersion into a bath of molten metal such as steel or iron.

The device 10 includes a support tube 12 which is typically made of a paperboard or like material. The support tube 12 is inserted into and surrounded by a high temperature protection sleeve 14. Positioned within the interior of the support tube 12 is a temperature sensing unit 16 having a body portion 18 and a thermocouple extension portion 20. The body protion 18 is positioned within the interior of the support tube 12 while the thermocouple extension portion 20 projects through and out of the end of the protection sleeve 14.

The protection sleeve 14 shown in the drawings is similar to that described in applicant's U.S. Pat. No. 4,645,865. The sleeve 14 is preferably vacuum casted from a fine refractory fiberous type material such as a ceramic type fiber as disclosed in U.S. Pat. No. 3,816,183. However, the sleeve 14 may take any specific form and is not limited to that shown by the drawing or by the patents discussed herein. The outer surface 22 of the protection sleeve 14 is preferably smooth. The interior of the protection sleeve 14 is provided with a generally cylindrical shaped bore 24 which extends from one end of the sleeve and terminates in a radial, inwardly projecting shoulder 26 which is formed adjacent to the immersion end 28 of the protection sleeve 14. Between the shoulder 26 and the immersion end 28 of the sleeve 14 is provided an inwardly tapering cylindrical surface 30 which tapers toward the immersion end 28 of the sleeve 14. This surface 30 forms a generally truncated cone shaped bore. A second shoulder 32 may be provided on the sleeve 14 which is open to the immersion end 28. The second shoulder 32 is in communication with the narrow end of the cone shaped bore 30.

The assembly of the device 10 is such that the body 18 of the temperature sensing unit 16 is inserted into the support tube 12 with the thermocouple extension portion 20 of the unit projecting away from the end of the tube 12. The support tube 12 and sensing unit 16 are inserted into the cylindrical bore 24 of the protection sleeve 14 such that the protection sleeve 14 and sensing unit 16 abut the inwardly projecting shoulder 26. This arrangement prepositions the projecting end of the sensing unit extension 20 beyond the immersion end 28 of the protection sleeve 14 by a predetermined amount. The cone shaped bore 30 and the second shoulder portion 32 of the protection sleeve 14 are filled with a refractory cement 34. The combination of the shoulder 26 and the cement fill 34 in the tapered bore 30 provides a positive locking of the temperature sensing unit 16 and the support tube 12 within the protection sleeve 14. Additionally, this arrangement provides an increased insulation of the temperature sensing unit 16 and permits the use of less refractory cement 34. The refractory sleeve 14 is typically a better insulator than the refractory cement 34, therefore the thermocouple unit 16 may be embedded in the sleeve at a relatively shallower depth. Additional advantages of this type structure are discussed in U.S. Pat. No. 4,645,865.

In accordance with the present invention the support tube 12 is provided with a reflective foil wrap 36. The reflective wrap 36 is provided in substantially direct contact with the exterior surface of the support tube 12. Additionally, the wrap 36 is folded over the end of the support tube 12 and is positioned around the legs 42 of the thermocouple extension 20 and over the top of the temperature sensing unit 16. The wrap 36 may be applied in any convenient manner and is preferably of an aluminum material approximately 0.004 inches thick, although other thicknesses may be utilized depending on design conditions. The outside surface of the wrap 36 is reflective of heat radiated from the protection sleeve 14 prior to and during immersion. The foil wrap 36 also acts as a heat sink for the heat transfered by conducting or convection from the sleeve 14 during immersion. The wrap 36, because of its relatively high conductivity, will also disperse absorbed heat from within the interior of the protection sleeve 14 substantially over its entire surface.

A common problem in the repeating temperature sensing devices 10 is the combustion of the paperboard material of the support tube 12 after a number of immersions. After repeated immersion of the device, the paperboard material of the tube 12 reaches its combustion point and combines with the oxygen within the interior of the cylindrical bore 24 to cause the paper to smolder or char. By providing a reflective foil wrap 36 of a non-combustible material in surrounding contact with the paperborad material the oxygen present within the cylindrical bore 24 is not directly exposed to the paperboard tube. Therefore, the wrap 36 prevents combustion of the tube 12 even at elevated temperature above its flash or burning point.

The body portion 18 of the temperature sensing unit 16 generally includes contacts 38 which extend from the end opposite from that of the thermocouple extension 20. The contacts 38 are adapted to mate with corresponding contacts on a lance (not shown) which is inserted through the support tube 12. The body portion 18 contains cold compensation joints between the thermocouple wire and the contacts 38 (structure not shown). In FIG. 2, a cross section of the body portion 18 is shown including a refractory cement fill 40. This refractory cement 40 acts to support the thermocouple extension portion 20 on the body portion 18 and protect the thermocouple wires and the cold joints within the body 18. The refractory cement fill 40 is, preferably, of the same material as refractory cement 34.

The thermocouple extension portion 20 of the sensing unit 16 typically comprises a U-shaped quartz type tube 42 which contains the hot junction of the thermocouple wire at the projecting end of the U-shape. A primary reason for failure of known variations of a repeating immersion device is due to the failure of the quartz material of this U-shaped tube 42. As part of the invention, the quartz tube 42 was modified by coating 44 the quartz material with an alumina ($AL_2O_3$) material which is then force-dried. The alumina coating 44 of the quartz tube 42 acts to strengthen the quartz material and prevent degradation during repeated immersions. Typically, the environment of the molten metal bath causes the quartz material to become soft and eventually fail. It has been discovered that by coating 44 the quartz material with the alumina in diluted strength (260 grams $AL_2O_3$ with 340 cc of a polyvinyl alcohol solution) that the failure of the quartz U-shaped tube is eliminated as a mode of failure of the device 10.

As stated previously, it was known to use an alumina coating on a quartz thermocouple tube on an oxygen and temperature type measuring device having an electrochemical cell for measuring the oxygen content in the bath. The application of the alumina coating in this type temperature and oxygen device is to prevent dissociation of the oxygen from the quartz which may effect the measurements of the oxygen sensing cell. In the present application, the alumina coating is provided in diluted strength as compared to previous uses 1000 grams $AL_2O_3$ with 400 cc polyvinyl alcohol) so that the alumina does not effect the response time of the thermocouple. By providing this coating on a repeating immersion temperature sensing device 10, the molten metal bath will not cause degradation of the quartz material after repeated immersions. The temperature and oxygen sensing type probes are not utilized for repeated immersions.

The structure of the immersion device 10 as shown in the drawings and as described herein substantially increases the useful life of the temperature sensing device described in U.S. Pat. No. 4,645,865. Each of the improvements as described herein substantially increase this useful life. However, each improvement may be utilized individually as desired.

Optional structure which may be added to the device 10 includes a cap located at the immersion end 28 of the sleeve to protect the thermocouple extension portion 20 during initial immersion of the device 10 through the slag on the top of the molten metal bath. Additionally, ribs 48 may be provided within the sleeve 14 which project inwardly from the cylindrical bore 24 so as to maintain the support tube 12 and temperature sensing unit 16 within the protection sleeve 14 in a fixed relationship. The cylindrical bore end of the sleeve 14 may be sealed by a refractory material (not shown). However, the device 10 contemplated by this invention is generaly not immersed into the bath beyond the level of the non-immersion end.

The invention as described herein substantially increases the useful life of a temperature sensing device such that the number of immersions, providing accurate temperature readings, may be increased. Testing has shown that the invention as described increases the number of immersions by two-fold.

The present invention may be embodied in other specific forms without departing from the spirit or essential attributes thereof and, accordingly, reference should be made to the appended claims, rather than to the foregoing specification, as indicating the scope of the invention.

We claim:

1. A temperature sensing device suitable for repeated immersion into a molten metal bath comprising: a protection sleeve made of a fibrous refractory material capable of withstanding repeated immersions into a molten metal bath having a central longitudinally extending bore therethrough; a support tube within the bore of the protection sleeve; and a thermocouple unit having a body portion supported by the support tube within one end thereof and a thermocouple extension portion extending from the body portion through the end of the protection sleeve, the support tube wrapped with a reflective foil material which substantially covers the entire surface of the support tube within the protection sleeve.

2. A temperature sensing device as claimed in claim 1 wherein the thermocouple extension portion of the sensing unit includes a U-shaped quartz tube, the U-shaped quartz tube having a coating over at least its surface area to be exposed to the molten metal upon immersion, the coating comprising an alumina material.

3. A temperature sensing device as claimed in claim 2 wherein said alumina material coating is made of a mixture in solution of approximately 260 grams $AL_2O_3$ and 340 cc of polyvinyl alcohol.

4. The temperature sensing device as claimed in claim 1 wherein the body portion of the sensing unit includes a refractory cement fill.

5. A temperature sensing device as claimed in claim claim 1 wherein the reflective foil wrap is an aluminum material.

6. A temperature sensing device as claimed in claim 5 wherein the aluminum foil wrap is approximately 0.004 inches in thickness.

7. A temperature sensing device as claimed in claim 1 wherein the reflective foil wrap encases the end portion of the support tube and the body portion of the sensing unit.

8. A temperature sensing device suitable for repeated immersion into a molten metal bath comprising: a generally cylindrical inert refractory protection sleeve; a cylindrical support tube within a generally cylindrical bore through the protection sleeve; and a thermocouple unit having a body portion supported by the support tube within one end thereof and a thermocouple extension portion extending away from the body portion through the end of the protection sleeve, the thermocouple extension portion including a U-shaped tube, and the U-shaped tube encasing the hot junction of the thermocouple unit, the U-shaped tube being made of a quartz material, and the quartz material being coated with an alumina type material over its surface area to be exposed to molten metal during immersion.

9. The temperature sensing device as claimed in claim 8 wherein the body portion of the sensing unit includes a refractory cement fill.

10. The temperature sensing device as claimed in claim 8 wherein the alumina material is made of a mixture in solution of approximately 260 grams of $AL_2O_3$ and 340 cc of a polyvinyl alcohol.

11. A temperature sensing device suitable for repeated immersion into a molten metal comprising: a generally cylindrical inert refractory sleeve, a generally cylindrical bore beginning at one end of the refractory sleeve and terminating at an inwardly projecting shoulder formed within the sleeve, a generally truncated cone-shaped bore within the sleeve being in axial alignment with the cylindrical bore and initiating at the inwardly projecting shoulder within the sleeve with the base of the truncated cone being adjacent to and in communication with the generally cylindrical bore and the opposite end of the truncated cone-shaped bore being in communication with the opposite end of the sleeve; a cylindrical support tube positioned within the generally cylindrical bore, one end of the support tube abutting the shoulder within the sleeve; a thermocouple unit having a body portion supported by said support tube within the end abutting the shoulder portion of the sleeve and a projecting member which extends from the body portion through the generally truncated cone-shaped bore of the sleeve, the projecting member extending beyond the end of the sleeve by a predetermined amount, the projecting member including a generally U-shaped quartz tube having a hot junction of the thermocouple contained therein, the quartz tube having a dilute alumina coating over its surface area to be exposed to molten metal upon immersions, the body portion supporting the U-shaped tube by means of a refractory cement fill; a refractory cement surrounding a portion of the projecting member of the thermocouple unit within the truncated cone-shaped bore and filling the truncated cone-shaped bore; and a refractory foil wrap surrounding the periphery and the end of the cylindrical support tube within the generally cylindrical bore of the protection sleeve; whereby the temperature sensing device may be immersed into a molten metal bath repeatedly while providing an increased number of temperature readings.

* * * * *